(12) United States Patent
Vial

(10) Patent No.: US 7,846,890 B2
(45) Date of Patent: Dec. 7, 2010

(54) PERFUMING INGREDIENTS CAPABLE OF IMPARTING WOODY ODORS

(75) Inventor: Christian Vial, Lathoy (FR)

(73) Assignee: Firmenich SA, Geneva (CH)

( * ) Notice: Subject to any disclaimer, the term of this patent is extended or adjusted under 35 U.S.C. 154(b) by 1206 days.

(21) Appl. No.: 11/471,328

(22) Filed: Jun. 19, 2006

(65) Prior Publication Data
US 2006/0241014 A1    Oct. 26, 2006

Related U.S. Application Data

(63) Continuation of application No. PCT/IB2004/003981, filed on Nov. 30, 2004.

(30) Foreign Application Priority Data
Jan. 27, 2004    (WO) ................ PCT/IB2004/000178

(51) Int. Cl.
*A61Q 13/00*    (2006.01)
*C11B 9/00*    (2006.01)
(52) U.S. Cl. ............................................ 512/25; 512/1
(58) Field of Classification Search ..................... 512/1, 512/25
See application file for complete search history.

(56) References Cited

U.S. PATENT DOCUMENTS 3,839,232 A    10/1974    Ohloff et al. ................. 252/522
4,511,496 A *  4/1985    Matsumoto ..................... 512/4

OTHER PUBLICATIONS

Nagaham, S. "Terpenoids. IX. Permanganate Oxidation of Thujopsene. Neutral Products," Bulletin of the Chemical Society of Japan, vol. 60, No. 11 (1987) pp. 4175-4177.*
G. Ohloff et al., XP009046247 "68. Uber En-Synthesen Mit Suingulett-Sauerstooff [1] II. Die Farbstoff-Sensibilisierte Photooxygenierung von (—)-Thujopsen Und Die Stereochemie Der Dargestellten Thujopsanole", Helvetica Chimica Acta—vol. 53, Fasc. 3, pp. 623-637 (1970).
P.C. Traas et al., xp009046242, "Peroxidation and Bromination of Thujopsene", Recueil, Journal of the Royal Netherlands Chemical Society, vol. 93, No. 9-10, pp. 264-269 (1974).

* cited by examiner

*Primary Examiner*—James Seidleck
*Assistant Examiner*—Saira Haider
(74) *Attorney, Agent, or Firm*—Winston & Strawn LLP

(57) ABSTRACT

The present invention relates to the field of perfumery and concerns a diether or a 1,3-dioxolane derivative of 1,8a-methano-2,4a,8,8-tetramethyldecahydro-2,3-naphthalene-diol and its use as perfuming ingredient. The present invention concerns also the perfuming compositions or perfumed articles associated with the compound.

15 Claims, No Drawings

PERFUMING INGREDIENTS CAPABLE OF IMPARTING WOODY ODORS

CROSS-REFERENCE TO RELATED APPLICATIONS

This application is a continuation of International application PCT/IB2004/003981 filed Nov. 30, 2004, the entire content of which is expressly incorporated herein by reference thereto.

TECHNICAL FIELD

The present invention relates to the field of perfumery. More particularly, it concerns a 1,8a-methano-2,4a,8,8-tetramethyldecahydro-2,3-naphthalenediol derivative of formula (I), as defined below, and its use as perfuming ingredient.

BACKGROUND

To the best of our knowledge, only two compounds of formula (I) are known from the prior art. Said compounds are the 3-acetate of [1aR-(1aα,2β,3β,4aβ,8aS)]-decahydro-2,4a,8,8-tetramethyl-cyclopropa[d]naphthalene-2,3-diol, and the 2-acetate of (1aR,2S,3S,4aS,8aS)-decahydro-2,4a,8,8-tetramethyl-cyclopropa[d]naphthalene-2,3-diol which are reported as intermediate compounds in the oxidation of thujopsene (e.g. see G. Ohloff et al. in Helv. Chem. Acta 1970, 623 or G. Ohloff et al. in Recueil des Travaux Chimiques des Pays-Bas, 1974, 93, 264). However, none of the prior art documents mentions or suggests that said compounds can be used as perfuming ingredients. The other compounds of formula (I) are new.

The closest analog, which is reported in the prior art as a perfuming ingredient, is 4,7,11,11-tetramethyl-tricyclo [5.4.0.0(1,3)]undecan-5-one disclosed in U.S. Pat. No. 3,839,232. Said document does not suggest that the compounds of the present invention are also useful perfuming ingredients.

SUMMARY OF THE INVENTION

The present invention now relates about the derivatives of 1,8a-methano-2,4a,8,8-tetramethyldecahydro-2,3-naphthalenediol, of formula (I) as defined below, their use as perfuming ingredient, as well as the perfuming compositions or articles associated with such compounds.

DETAILED DESCRIPTION OF THE PREFERRED EMBODIMENTS

Surprisingly, we have now established that the 1,8a-methano-2,4a,8,8-tetramethyl-decahydro-2,3-naphthalenediol derivative of formula

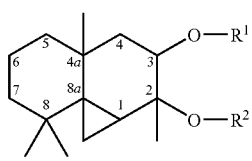

(I)

wherein $R^1$ or $R^2$, taken separately, represents each a $C_{1-3}$ alkyl group or a $COR^3$ group, $R^3$ representing a methyl or ethyl group, and one of said $R^1$ or $R^2$ may also represent a hydrogen atom; or said $R^1$ and $R^2$, taken together, represent a $C(R^4)_2$ group, each $R^4$ representing a hydrogen atom, a $C_{1-3}$ alkyl group or, taken together, a $CH_2$—$(CH_2)_2$—$CH_2$ or $CH_2$—$(CH_2)_3$—$CH_2$ group; in the form of any one of its isomers or of a mixture thereof, possesses a very useful woody-ambery type fragrance, which renders them very convenient for the preparation of perfuming compositions and perfumed products.

According to a particular embodiment of the invention, $R^1$ or $R^2$, taken separately, represents each a $C_{1-3}$ alkyl group and one of said $R^1$ or $R^2$ may also represent a hydrogen atom, or said $R^1$ and $R^2$, taken together, represent a $C(R^4)_2$ group, each $R^4$ representing a hydrogen atom or a $C_{1-3}$ alkyl group or, taken together, a $CH_2$—$(CH_2)_2$—$CH_2$ or $CH_2$—$(CH_2)_3$—$CH_2$ group.

A preferred compound of the invention is the (1R,4aS,8aS)-1,8a-methano-2,4a,8,8-tetramethyldecahydro-2,3-naphthalenediol derivative of formula

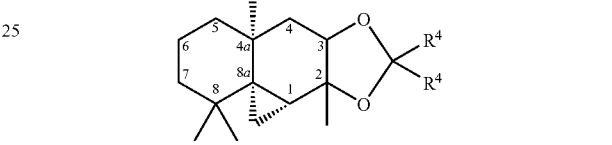

(II)

wherein each $R^4$ represents, independently from the other, a hydrogen atom or a $C_{1-3}$ alkyl group, preferably a methyl group. As previously, compound of formula (I) may also be in the form of any one of its isomers or in the form of a mixture of said isomer.

A typical example of the invention's compounds is (1R,4aS,8aS)-2,3-(dimethylmethylenedioxy)-1,8a-methano-2,4a,8,8-tetramethyldecahydronaphthalene, the odor of which being characterized by a substantive woody-ambery character, which is in the same direction of the one of 1-(2,2,3,6-tetramethyl-cyclohexyl)-3-hexanol but is less dry, more cedar and sweeter. Moreover the odor of said invention's compound is also characterized by the presence of floral-red fruit notes, which are very surprising for a compound belonging to the woody-ambery olfactive family. Said floral-fruity notes can contribute in a very positive and non-conventional manner to the odor of the accords, perfumes, into which the invention compound is added.

Another example of compound (II) is (1R,2R,3S,4aS,8aS)-2,3-(dimethylmethylenedioxy)-1,8a-methano-2,4a,8,8-tetramethyldecahydronaphthalene which has an odor very close to the one of the (1R,4aS,8aS) isomer, mentioned above, but which shows an additional "lait de santal" note. Said (1R,2R,3S,4aS,8aS) isomer imparts a very similar odor, but having a stronger intensity, when compared with its diastereomer of configuration (1R,2S,3R,4aS,8aS).

The invention's compounds can be easily prepared by oxidation of thujopsene into the corresponding diol, e.g. by standard means such as $OSO_4$. The diol thus obtained is subsequently transformed into the invention's acetal, ester or ether according to any standard procedure for such chemical transformation. A specific example is provided in the Examples.

Due to the surprising properties of the compounds of formula (I), another object of the present invention is a perfuming composition comprising i) at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet an encapsulating materials. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, then other suitable perfumery carrier, than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I) or an invention's composition; and
ii) a consumer product base, is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 5% by weight, can be used when these compounds are incorporated into perfumed articles.

As mentioned above, the invention concerns also the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)", it has to be understood here also the use of an invention's composition.

EXAMPLES

The following example are further illustrative of the present invention's embodiments and further demonstrate the advantages of the invention relative to the prior art. The abbreviations have the usual meaning in the art, the temperatures are indicated in degrees centigrade (° C.); the NMR spectral data were recorded in CDCl$_3$ (if not stated otherwise) with a 500 or 125 MHz machine for $^1$H or respectively $^{13}$C, the chemical displacement δ are indicated in ppm with respect to the TMS as standard, the coupling constants J are expressed in Hz.

Example 1

Preparation of Compounds of Formula (II)

a) Synthesis of (1R,4aS,8aS)-1,8a-methano-2,4a,8,8-tetramethyldecahydro-2,3-naphthalenediol In a 1000 ml round bottomed flask were placed 97 g (0.475 mole) of thujopsene (GC purity=74%, [α]$^D_{20}$=−78.0° (2.8% in CHCl$_3$)), 338 ml of $^t$BuOH, 37.5 ml of pyridine, 69 ml of demineralized water, 62.5 g (0.562 mole) of trimethylamine oxide trihydrate and 10 g of 2.5% OsO$_4$ in $^t$BUOH. The mixture was heated at reflux for 12 days and, after cooling, poured into a solution of 15.6 g Na$_2$S$_2$O$_3$ in 1200 ml of water. The mixture was extracted three times with ether (150 ml) and the organic phases were washed twice with 10% HCl (50 ml), twice with saturated NaHCO$_3$ (50 ml) and water (50 ml). After concentration, 115.0 g of desired diol (GC purity: 64%) were obtained and used without further purification.

The physical data of the diol correspond to the one already reported in the prior art.

b) Synthesis of (1R,4aS,8aS)-2,3-(dimethylmethylenedioxy)-1,8a-methano-2,4a,8,8-tetramethyl-decahydronaphthalene and Isolation of the Diastereomers of Configuration (1R,2R,3S,4aS,8aS) and (1R,2S,3R,4aS,8aS)

To a solution of 115.0 g of the diol obtained under a) in 1000 ml of 2,2-dimethoxypropane were added 5 g of p-toluenesulfonic acid. After stirring 4 hours at room temperature the mixture was diluted with 200 ml of ether and 500 ml of pentane, then washed subsequently with water, saturated NaHCO$_3$ and water, dried on Na$_2$SO$_4$ and concentrated to give a residue. The latter was rapidly distilled using a distillation head (Eb$_{(0.13\ mbar)}$=60-85°) to give crude (1R,4aS, 8aS)-2,3-(dimethylmethylenedioxy)-1,8a-methano-2,4a,8, 8-tetramethyldecahydronaphthalene (purity: 67%). Said crude compound was further purified by a first distillation using a Fischer column MS 300 (Eb$_{(0.1\ mbar)}$=35-72°, 35.4 g) and a second distillation, using a distillation head (Eb$_{(0.18\ mbar)}$=72-84°), to give 75.48 g (yield=52%) of (1R, 4aS,8aS)-2,3-(dimethylmethylenedioxy)-1,8a-methano-2, 4a,8,8-tetramethyldecahydro-naphthalene (purity: 90%).

A flash chromatography (silica, pentane/ether=9:1) of (1R, 4aS,8aS)-2,3-(dimethylmethylenedioxy)-1,8a-methano-2, 4a,8,8-tetramethyldecahydronaphthalene provided the pure isomers (1R,2R,3S,4aS,8aS) and (1R,2S,3R,4aS,8aS).

(1R,2S,3R,4aS,8aS)-2,3-(dimethylmethylenedioxy)-1,8a-methano-2,4a,8,8-tetramethyldecahydronaphthalene mp 116-117° [α]$^D_{20}$=−15.5° (1.6% in CHCl$_3$)
MS: M$^+$ 278(3), 263(52), 235(12), 220(71), 203(80), 187 (23), 177(27), 161(24), 147(41), 135(86), 123(78), 111(100), 95(63), 81(48), 69(54), 55(48), 43(74).
$^1$H-NMR: −0.09 (dd: J$_1$≈J$_2$=5.6, 1H), 0.40 (dd: J$_1$=10.6, J$_2$=5.6, 1H), 0.61 (s, 3H), 1.02 (s, 3H), 1.06 (s, 3H), 1.17 (dd: J$_1$=15.7, J$_2$=2.9, 1H), 1.26 (m, 1H), 1.32 (s, 3H), 1.33 (s, 3H), 1.36 (m, 2H), 1.47 (m, 3H), 1.51 (s, 3H), 1.73 (m, 1H), 2.52 (ddd: J$_1$≈J$_2$=13.5, J$_3$=3.8, 1H), 3.81 (dd. J$_1$≈J$_2$=2.9, 1H).
$^{13}$C-NMR: 8.6 (t), 19.3 (t), 26.0 (q), 27.0 (q), 27.1 (q), 28.0 (q), 29.3 (q), 29.5 (q), 29.7 (d), 31.2 (s), 32.4 (s), 33.5 (s), 37.2 (t), 38.1 (t), 40.9 (t), 78.2 (s), 78.3 (d), 106.9 (s).

(1R,2R,3S,4aS,8aS)-2,3-(dimethylmethylenedioxy)-1,8a-methano-2,4a,8,8-tetramethyldecahydronaphthalene Eb$_{(0.03\ mbar)}$=120° [α]$^D_{20}$=−33.80 (1.2% in CHCl$_3$)
MS: M$^+$ 278(1): 263(40), 235(3), 221(35), 203(42), 187 (5), 178(26), 163(38), 147(19), 135(52), 123(100), 107(65), 95(47), 81(41), 69(42), 55(40), 43(66).
$^1$H-NMR: 0.52 (dd: J$_1$=10.2, J$_2$=5.6, 1H), 0.60 (dd: J$_1$≈J$_2$=5.6, 1H), 0.61 (s, 3H), 1.07 (s, 3H), 1.12 (s, 3H), 1.14-1.38 (m, 5H), 1.40 (s, 3H), 1.43 (s, 3H), 1.49 (m, 3H), 1.54 (s, 3H), 1.80 (m, 1H), 3.93 (dd: J$_1$=11.8, J$_2$=7, 1H).
$^{13}$C-NMR: 9.2 (t), 18.9 (t), 27.0 (q), 28.7 (d), 29.0 (q), 29.4 (q), 29.5 (q), 30.2 (q), 31.4 (q), 33.6 (s), 34.6 (s), 35.2 (s), 36.4 (t), 40.9 (t), 42.8 (t), 77.7 (d), 79.4 (s), 108.1 (s).

Example 2

Preparation of a Perfuming Composition

An accord of the "wild strawberry" type was prepared by admixing the following ingredients:

| Ingredient | Parts by weight |
| --- | --- |
| 10%* Acetaldehyde | 30 |
| Amylcinammic Aldehyde | 1000 |
| Hexanal[1)] | 5 |

-continued

| Ingredient | Parts by weight |
|---|---|
| Octanal[1] | 10 |
| Allyl Caproate | 200 |
| 10%* 1-Octen-3-ol | 20 |
| Methyl Cinnamate | 25 |
| Ethylmaltol | 500 |
| Damascone Alpha[1] | 100 |
| 8-Methoxy-1-P-menthene | 1000 |
| Fructalate ®[2] | 400 |
| Furaneol ®[3] | 100 |
| Habanolide ®[4] | 1000 |
| Iralia Total ®[5] | 300 |
| Isopropyl 2-methylbutanoate | 500 |
| Ethyl 2,3-epoxy-3-phenylbutanoate | 2550 |
| Hedione ®[6] | 1000 |
| 1%* Dimethyl sulfide | 10 |
| Neobutenone ®[7] | 50 |
| (Z)-3-Hexen-1-ol | 100 |
| Terpinolene | 300 |
| 2,4-Dimethyl-3-cyclohexene-1-carbaldehyde | 300 |
| | 9500 |

*in dipropyleneglycol
[1])Origin: Firmenich SA, Switzerland
[2])Diethyl 1,4-cyclohexane dicarboxylate; origin: Firmenich SA, Switzerland
[3])4-Hydroxy-2,5-dimethyl-3(2H)-furanone; origin: Firmenich SA, Switzerland
[4])Pentadecenolide; origin: Firmenich SA, Switzerland
[5])Methyl ionone; origin: Firmenich SA, Switzerland
[6])Methyl dihydrojasmonate; origin: Firmenich SA, Switzerland
[7])1-(5,5-Dimethyl-1-cyclohexen-1-yl)-4-penten-1-one; origin: Firmenich SA, Switzerland The addition of 500 parts by weight of (1R,4aS,8aS)-2,3-(dimethylmethylenedioxy)-1,8a-methano-2,4a,8,8-tetramethyldecahydronaphthalene to the above-described accord imparted to the latter a distinctly natural aspect, by enhancing the fruity notes. The addition of the invention's compound to the accord had also the effect of providing a scent which was much more round, agreeable and with an enhanced volume and diffusion. The overall effect could not be achieved by the addition of one of the prior art perfuming ingredients belonging to the same woody-ambery family.

Example 3

Preparation of a Perfuming Composition

An accord for man, of the "green-floral-woody" type was prepared by admixing the following ingredients:

| Ingredient | Parts by weight |
|---|---|
| Benzyl Acetate | 10 |
| Bergamot essential oil | 20 |
| Cetalox ®[1] | 15 |
| Citronellol | 30 |
| 3-(4-Isopropylphenyl)-2-methylpropanal | 8 |
| Damascone Alpha[2] | 2 |
| Dihydromyrcenol | 330 |
| 2-Methyl-1-phenyl-2-propanol | 20 |
| Galbex 183 ®[2] | 25 |
| Geraniol | 15 |
| 50%* Habanolide ®[3] | 150 |
| Hedione ®[4] | 35 |
| Iso E Super ®[5] | 200 |
| Lilial ®[6] | 150 |
| Linalol | 25 |
| Phenylethyl Alcohol | 25 |
| Polysantol ®[7] | 15 |

-continued

| Ingredient | Parts by weight |
|---|---|
| Styrallyl Acetate | 15 |
| Vertofix Coeur ®[8] | 200 |
| | 1290 |

*in dipropyleneglycol
[1])8,12-Epoxy-13,14,15,16-tetranorlabdane; origin: Firmenich SA, Switzerland
[2])Origin: Firmenich SA, Switzerland
[3])Pentadecenolide; origin: Firmenich SA, Switzerland
[4])Methyl dihydrojasmonate; origin: Firmenich SA, Switzerland
[5])1-(Octahydro-2,3,8,8-tetramethyl-2-naphtalenyl)-1-ethanone; origin: IFF, USA
[6])3-(4-Tert-butylphenyl)-2-methylpropanal; origin: Givaudan SA, Switzerland
[7])3,3-Dimethyl-5-(2,2,3-trimethyl-3-cyclopenten-1-yl)-4-penten-2-ol; origin: Firmenich SA, Switzerland
[8])Methyl cedryl ketone; origin: IFF, USA The addition to the above-described accord of 10 parts by weight of a 1% w/w solution of (1R,4aS,8aS)-2,3-(dimethylmethylenedioxy)-1,8a-methano-2,4a,8,8-tetramethyldecahydronaphthalene in dipropyleneglycol resulted in a new accord having a unique and very cosmetic note that was attributed to floral and fruity aspects combined with the woody and amber characteristics of the invention's compound.

As in Example 2, the new accord had an improved volume and diffusion as well as a much more round and agreeable scent. This result was not achieved by the addition of other known perfuming ingredients such as 2-cyclododecyl-1-propanol or (−)-(1R,3S,7R,8R,10S,13R)-5,5,7,9,9,13-hexamethyl-4,6-dioxatetracyclo[6.5.1.0 (1,10).0(3,7)]tetradecane which, while contributing to the woody and amber aspects of the accord, did not introduce any unique or interesting effects to the floral notes or to the diffusion of the scent.

Example 4

Preparation of a Perfuming Composition

An accord of the "pine" type was prepared by admixing the following ingredients:

| Ingredient | Parts by weight |
|---|---|
| Decanal[1] | 5 |
| Dodecanal | 10 |
| Dihydromyrcenol | 150 |
| Eucalyptus Oil | 100 |
| Farenal ®[2] | 5 |
| 3,7-Dimethyl-2,6-octadienitrile | 20 |
| Isobornyl Acetate | 520 |
| Menthone | 20 |
| 2-Methylundecanal[1] | 20 |
| 10%* Neobutenone ®[3] | 10 |
| Peppermint Oil | 20 |
| Scentenal ®[4] | 80 |
| 10%* (E)-4-Decenal[5] | 5 |
| 2,4-Dimethyl-3-cyclohexene-1-carbaldehyde | 10 |
| | 975 |

*in dipropyleneglycol
[1])Origin: Firmenich SA, Switzerland
[2])2,6,10-trimethyl-9-undecenal; origin Symrise, Germany
[3])1-(5,5-Dimethyl-1-cyclohexen-1-yl)-4-penten-1-one; origin: Firmenich SA, Switzerland
[4])8(9)-Methoxy-tricyclo[5.2.1.0.(2,6)]decane-3(4)-carbaldehyde; origin: Firmenich SA, Switzerland
[5])Origin: Givaudan SA, Switzerland The addition to the above-described accord of 25 parts by weight of a 10% w/w solution of (1R,4aS,8aS)-2,3-(dimethylmethylenedioxy)-1,8a-methano-2,4a,8,8-tetramethyl-decahydronaphthalene in dipropyleneglycol resulted in a new accord having a reinforced woody and amber character and a unique a delicate floral and fruity aspects.

The woody-amber character was less dry, and more rounded than the one provided by the addition of other perfuming ingredients capable of imparting said notes.

What is claimed is:

1. A compound of formula

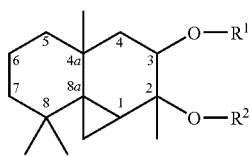
(I)

wherein $R^1$ or $R^2$, taken separately, represents each a $C_{1-3}$ alkyl group or a $COR^3$ group, $R^3$ representing a methyl or ethyl group, and one of said $R^1$ or $R^2$, but not both, may also represent a hydrogen atom; or said $R^1$ and $R^2$, taken together, represent a $C(R^4)_2$ group, each $R^4$ representing a hydrogen atom, a $C_{1-3}$ alkyl group or, taken together, a $CH_2$—$(CH_2)_2$—$CH_2$ or $CH_2$—$(CH_2)_3$—$CH_2$ group;

in the form of any one of its isomers or of a mixture thereof, provided that the 3-acetate of [1aR-(1aα,2β,3β,4aβ,8aS)]-decahydro-2,4a,8,8-tetramethyl-cyclopropa[d]naphthalene-2,3-diol and the 2-acetate of (1aR,2S,3S,4aS,8aS)-decahydro-2,4a,8,8-tetramethyl-cyclopropa[d]naphthalene-2,3-diol are excluded.

2. A compound according to claim 1, wherein the compound is of formula

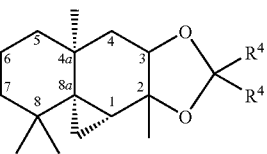
(II)

wherein each $R^4$ represents, independently from the other, a hydrogen atom or a $C_{1-3}$ alkyl group.

3. A perfuming composition comprising:
  i) at least one compound according to claim 1;
  ii) at least one ingredient selected from the group consisting of a perfumery carrier and a perfumery base; and
  iii) optionally at least one perfumery adjuvant.

4. A perfumed article comprising:
  i) as perfuming ingredient, at least one compound according to claim 1; and
  ii) a consumer product base.

5. A perfumed article according to claim 4, in the form of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

6. A perfumed article comprising:
  i) as perfuming ingredient, a composition according to claim 3; and
  ii) a consumer product base.

7. A perfumed article according to claim 6, in the form of a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. A method to confer, enhance, improve or modify the odor properties of a perfuming composition or of a perfumed article, which method comprises adding to said composition or article an effective amount of at least a compound of formula (I) as defined in claim 1.

9. A method to confer, enhance, improve or modify the odor properties of a perfuming composition or of a perfumed article, which method comprises adding to said composition or article an effective amount of at least a compound of formula (I) as defined in claim 2.

10. (1R,4aS,8aS)-2,3-(dimethylmethylenedioxy)-1,8a-methano-2,4a,8,8-tetramethyldecahydronaphthalene, (1R,2R,3S,4aS,8aS)-2,3-(dimethylmethylenedioxy)-1,8a-methano-2,4a,8,8-tetramethyldecahydronaphthalene or (1R,2S,3R,4aS,8aS)-2,3-(dimethylmethylenedioxy)-1,8a-methano-2,4a,8,8-tetramethyldecahydronaphthalene.

11. The perfuming composition of claim 3, wherein the compound is (1R,4aS,8aS)-2,3-(dimethylmethylenedioxy)-1,8a-methano-2,4a,8,8-tetramethyldecahydronaphthalene.

12. The perfumed article of claim 4, wherein the compound is (1R,4aS,8aS)-2,3-(dimethylmethylenedioxy)-1,8a-methano-2,4a,8,8-tetramethyldecahydronaphthalene.

13. The method of claim 8, wherein the compound is (1R,4aS,8aS)-2,3-(dimethylmethylenedioxy)-1,8a-methano-2,4a,8,8-tetramethyldecahydronaphthalene.

14. A method to confer, enhance, improve or modify the odor properties of a perfuming composition or of a perfumed article, which method comprises adding to said composition or article an effective amount of at least a compound of formula (I) as defined in claim 10.

15. (1R,4aS,8aS)-2,3-(dimethylmethylenedioxy)-1,8a-methano-2,4a,8,8-tetramethyldecahydronaphthalene.

* * * * *